United States Patent [19]

Kurtz

[11] 4,093,382
[45] June 6, 1978

[54] HYBRID HOLOGRAPHIC NON-DESTRUCTIVE TEST SYSTEM

[75] Inventor: Robert L. Kurtz, Huntsville, Ala.

[73] Assignee: The United States of America as represented by the Administrator of the National Aeronautics and Space Administration, Washington, D.C.

[21] Appl. No.: 686,331

[22] Filed: May 14, 1976

[51] Int. Cl.² ............ G01N 21/00; G02B 27/00; G01N 3/00
[52] U.S. Cl. ............................. 356/72; 73/603; 350/3.5; 356/73
[58] Field of Search ............... 356/72, 73; 350/3.5; 73/67.5 H, 71.3; 340/5 H

[56] References Cited

U.S. PATENT DOCUMENTS

| | | | |
|---|---|---|---|
| 3,626,753 | 12/1971 | Aprahamian et al. | 350/3.5 |
| 3,883,215 | 5/1975 | Kurtz | 350/3.5 |

OTHER PUBLICATIONS

Hinsley, J. E. "Non-Destructive Testing," MacDonald & Evans Ltd., 1959, pp. 44–49.
Waters, J. P., "Holography," Chapt. 2 of Holographic Non-Destructive Testing, edited by R. K. Erf, Academic Press, 1974, pp. 34–39.
Marrone et al., "Dual Index Holographic Contour Mapping Over a Large Range of Contour Spacings," Applied Optics, 1-1975, pp. 23–24.
Kurtz et al., "Hybrid Design Provides HNDT with Automatic Data Processing," Holosphere, 4-1976, pp. 1-5.
Pernick, B. J., "Limits to The Detection of Small Internal Voids in Solids With Holographic Techniques," Applied Optics, 7-1974, pp. 1711–1722.
Pryor, T. R., "Diffractographic Applications to Non-Destructive Testing," Materials Evaluation, 7-1974, pp. 142–152.

*Primary Examiner*—John K. Corbin
*Assistant Examiner*—Wm. H. Punter
*Attorney, Agent, or Firm*—George J. Porter; John R. Manning; L. D. Wofford, Jr.

[57] ABSTRACT

An automatic hybrid holograhic non-destructive testing (HNDT) method and system capable of detecting flaws or debonds contained within certain materials. This system incorporates the techniques of optical holography, acoustical/optical holography and holographic correlation in determining the structural integrity of a test object. An automatic processing system including a detector and automatic data processor is used in conjunction with the three holographic techniques for correlating and interpreting the information supplied by the non-destructive systems. The automatic system also includes a sensor which directly translates an optical data format produced by the holographic techniques into electrical signals and then transmits this information to a digital computer for indicating the structural properties of the test object. The computer interprets the data gathered and determining whether further testing is necessary, as well as the format of this new testing procedure.

7 Claims, 5 Drawing Figures

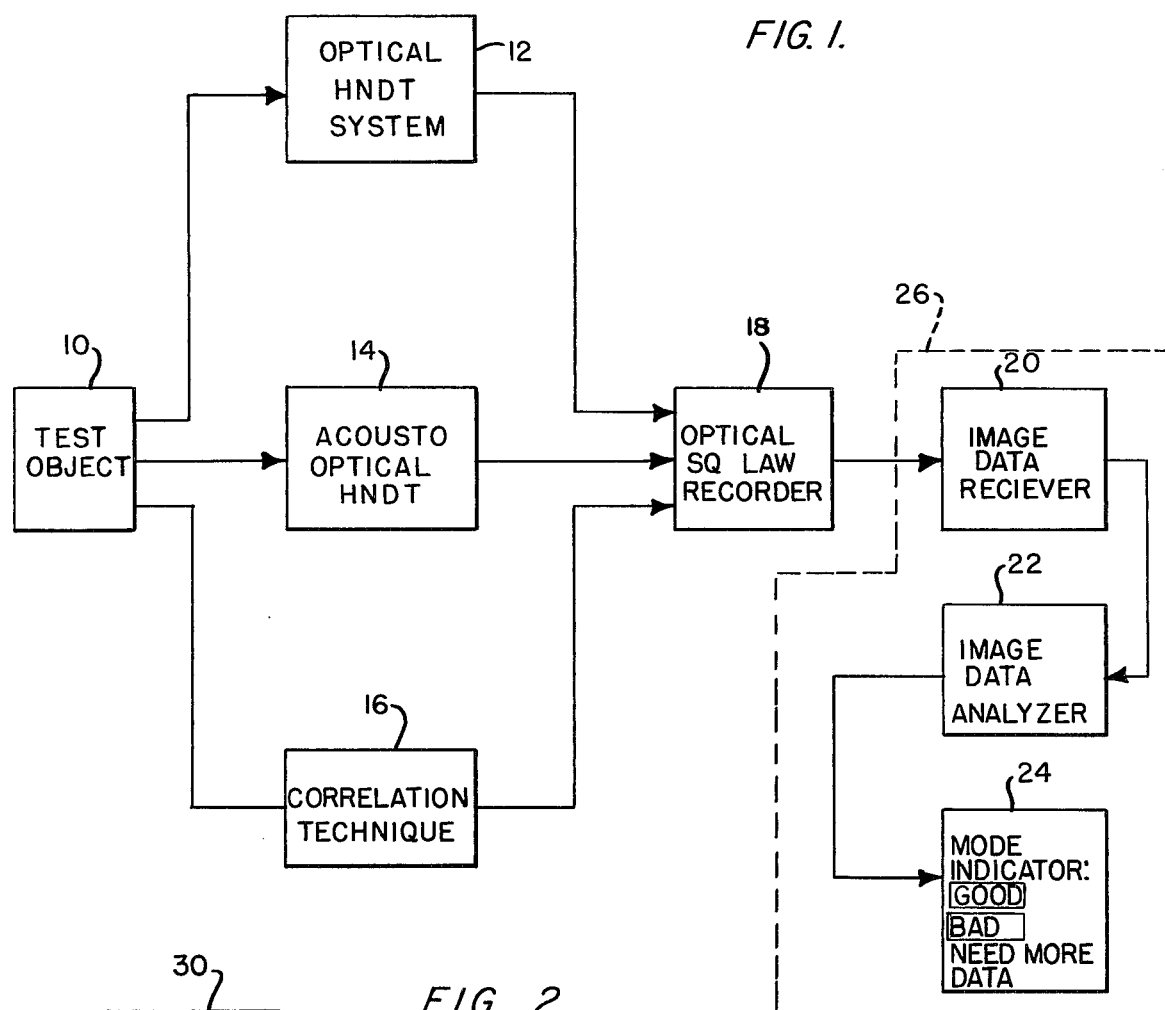
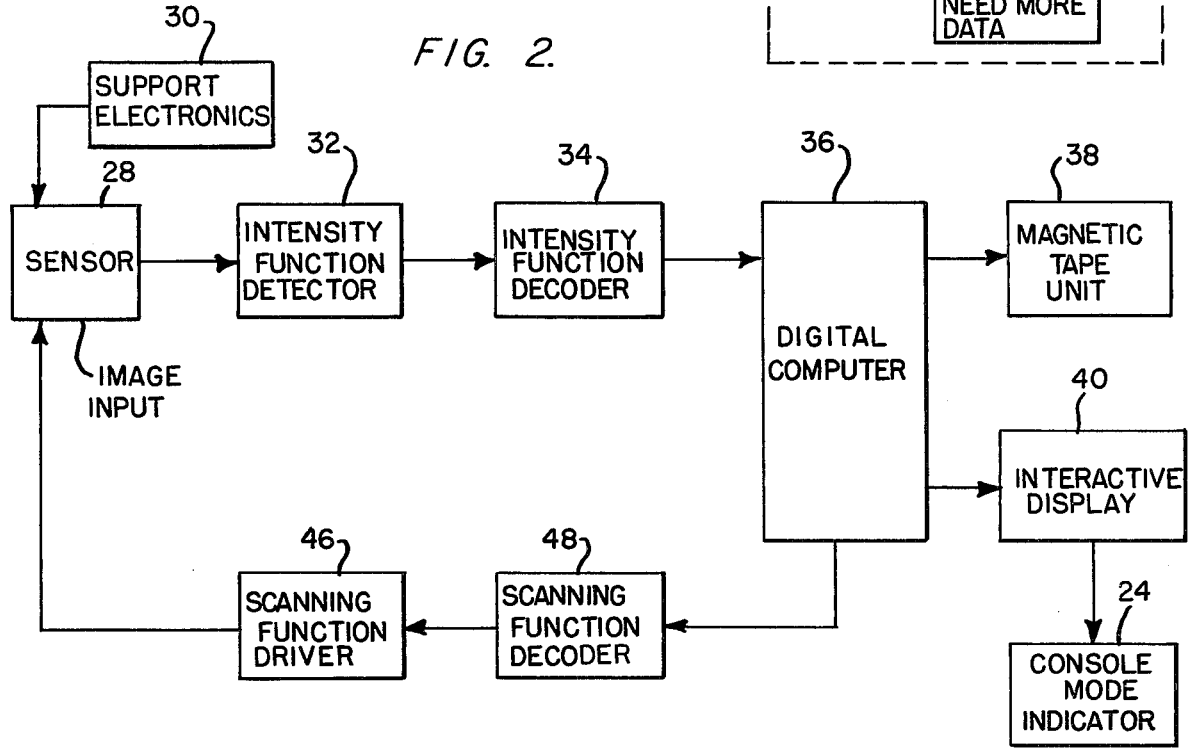

HYBRID HOLOGRAPHIC NON-DESTRUCTIVE TEST SYSTEM

ORIGIN OF THE INVENTION

The invention described herein is made by an employee of the United States Government and may be manufactured and used by or for the Government for governmental purposes without the payment of any royalties thereon or therefore.

FIELD OF THE INVENTION

The present invention relates to a holographic method and system for non-destructive testing of certain materials such as small optical components, printed circuits, automobile/airplane tires and rocket engines.

BACKGROUND OF THE INVENTION

With the advent of modern technology, the need has arisen for components and structures of uprecedented efficiency. Such structures require both a greatly improved understanding and exploitation of the engineering properties of classical materials plus the development and use of new materials, such as non-metallics and composites. Along with these developments, a need has arisen for commensurate improvements in the technology of holographic non-destructive testing (HNDT).

There presently exists a multitude of non-destructive testing techniques, each having its own applications, advantages and limitations. The primary limitation of each of these techniques is that they may only be used on certain test objects or to determine the presence of only certain flaws, debonds or inhomogeneities. Three of these techniques are the optical holography, acoustical holography and holographic correlation techniques. The optical holographic system is described in U.S. Pat. No. 3,883,215, issued to the present inventor, Robert Kurtz. This patent describes a holographic system for the sequential non-destructive testing utilizing a real time anaylsis method, a double exposure method and a time-averaging method all with the same optical system. This system can accommodate all forms, shapes, sizes and geometries of known objects which demand non-destructive testing. This then alleviated the need for many different arrangements of holographic systems, each one of which only accommodated individual materials and/or objects. However, because optical holography is dependent on a subsurface flaw or debond making its presence known by virtue of a concomitant change on the surface of the object, many of said flaws or debonds cannot be discovered by utilizing this technique alone.

Acoustical holography, on the other hand, has the advantage of utilizing long wavelength radiation and, consequently, materials normally opaque to the optical wavelengths are transparent to this wavelength region. Therefore, acoustical holography allows for the object to be inspected throughout its entire volume which would otherwise be impossible using optical holography. However, one of the prime disadvantages of acoustical holography is that of resolution in its detection and recording techniques. Therefore, to properly test certain objects, one would need to employ more than one technique and, consequently, one would then have to inspect more than one hologram and/or type of hologram of the same scene in order to obtain all of the positive information about the test objects.

The correlation technique has a very distinct advantage in flaw detection and has been employed repeatedly for such testing of printed circuit boards, etc. This technique basically operates on the principle of correlation of intensity returned from some small area of tests. The magnitude deviation of the returned intensity (of an optical beam) is a direct function of the location and magnitude of the surface change, i.e., or flaw. The disadvantage here is that it is restricted to operate over a relatively small area and, consequently, could not be well applied for inspection of large objects. Therefore, to properly test a large object, all three of these holographic techniques are necessary, and, consequently, a minimum of three separate holograms may have to be interpreted.

SUMMARY OF THE INVENTION

It is therefore an object of the present invention to overcome the defects of the prior art as mentioned above by formulating a technique which would employ the three above-named systems in such a way as to realize the respective advantages of each. The basic arrangement for this hybrid system would be that of the composite mobile holographic non-destructive test system embodied in U.S. Pat. No. 3,883,215. This would allow all of the concomitant advantages of that system such as variable sensitivity and mobility; and additionally, object testing in this system would provide interferometric fringe profiles whose analysis would be indicative of the presence of subsurface flaws, debonds and inhomogeneities. This test information would be recorded on an optical read-out hologram in the usual fashion.

To this basic system would be incorporated the ability to acoustically interrogate the interior of the object and the subsequent use of this acoustical information to acousto-optically modulate the optical object beam of the basic optical system. Once again, this modulated object beam would be recorded on an optical read-out hologram in the usual fashion. Object testing in this system would provide holographic information whose analysis would be sensitive to density changes within the structure of the object and thereby indicative of the presence of inhomogeneities such as flaws and debonds in the object structure.

The holographic correlation technique is employed in this compound system as a "fine tuning" technique for the further interrogation of the now recognized, localized flaws. Again, the holographic information is to be recorded on an optical read-out hologram.

According to the object which is to be tested, one of the holographic techniques discussed hereinabove will be initially employed to test said object for the presence of a defect or flaw. The output of this test is sensed and analyzed by a digital computer, said computer then indicating whether further data is necessary, and if so, which additional holographic techniques should be employed in the testing process.

BRIEF DESCRIPTION OF THE DRAWINGS

FIG. 1 is a flow chart of the entire hybrid system;

FIG. 2 is a flow chart of the optical sanner of the hybrid system;

DETAILED DESCRIPTION OF THE PREFERRED EMBODIMENT

Figure 3:
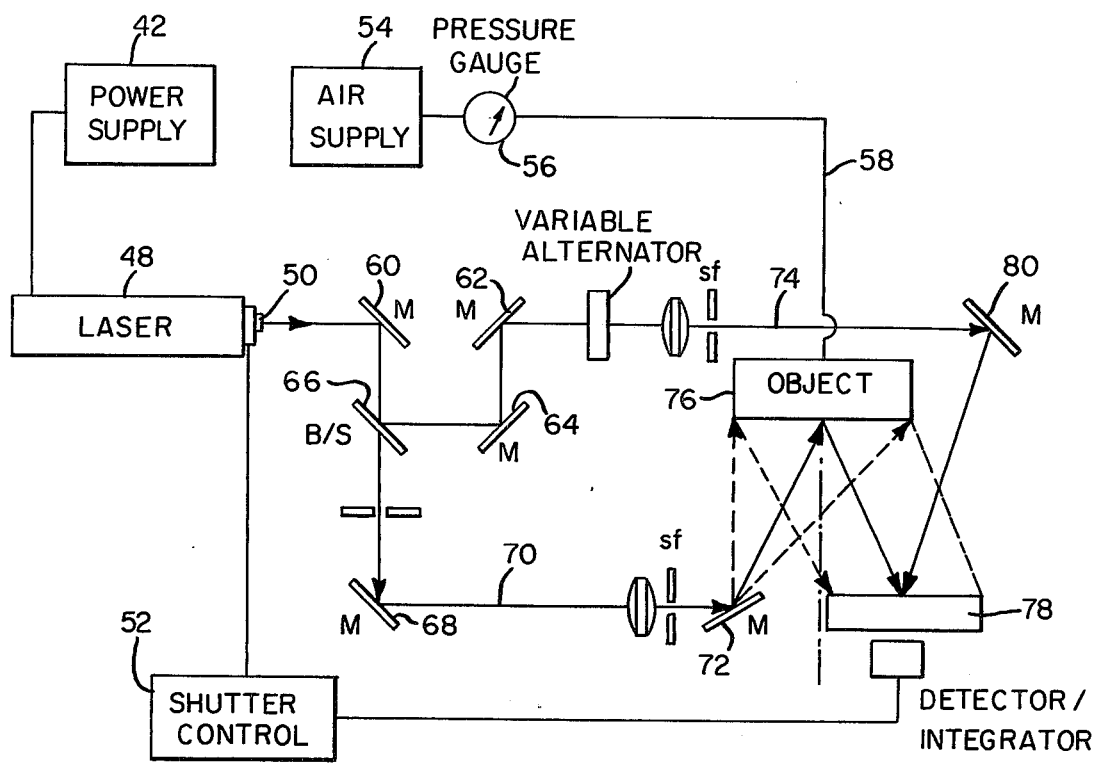
FIG. 3 is a schematic of an optical HNDT subsystem.

FIG. 1 shows a flow chart of the hybrid system in its current configuration. The object to be tested 10 may be investigated by an optical HNDT subsystem 12, an acousto-optical HNDT subsystem 14, or by a correlation technique 16, separately, or it may be sequentially investigated by one or more of these subsystems dependent on the type of test object and type of deformity sought. When the requirements of the test object necessitate the use of the optical HNDT subsystem, it will involve several modes of operation of this one subsystem, such as: the use of real time, double exposure or time-averaged type holography with; thermal, pressure or vibration type loading of the test object.

The output of these three subsystems is recorded on a standard optical square law recorder 18 in the form of an optical hologram. In all cases, for the optical holography, the data to be evaluated will be some form of interferometric fringe superposed on the holographic image of the test object 10.

When the requirements of the test object necessitate the use of the acousto-optical HNDT subsystem 14, conceivably there will again be several modes in which this subsystem could operate such as, for example, an immersion technique or a scanning technique. In this case, the acoustical information will be modulated onto an optical carrier, and again, an optical wavefront (holographic or photographic) will be recorded by the optical square law detector 18. In all cases, the data to be evaluated will be an optical image of the test object displaying a transparent view of this object and any internal deformities.

When the requirements of the test object necessitate the use of the correlation technique 16, then a Fourier transform hologram (a matched Vander Lugt filter) will be recorded of the test object in an unstressed state. The information recorded by the optical square law detector 18 will also be an optical hologram. In all situations, the data to be evaluated will be an intensity correlation between two wavefronts (unstressed and stressed) with this correlation being indicative of flaws or deformities in an area of interest on the test object.

Normally, the operation of this hybrid system will involve the sequential employment of all three of these subsystems on the test objects in the following manner: at the discretion of the operator and determined by the characteristics of the test object and the requirements of the deformity to be detected, one of the three holographic techniques will be used to test the test object. In most situations, the optical HNDT system 12 will be initially employed to obtain interferometric fringes of the test object in the unstressed and stressed state. Examination of these fringes, by an automatic processing system described in greater detail hereinbelow, would determine a range of (x,y) coordinates on the test objects which are suspect of flaws or deformities.

The analyzation of the fringes by the processing system would also indicate whether further testing of the object is warranted, and if so, which additional technique should be used, and under what specific conditions should the test be implemented. In some cases, the computer might indicate to perform the same technique twice in succession, but under different test conditions. Ordinarily, however, if the optical technique does not effectively isolate a subsurface flaw, if this technique is initially employed, the acousto-optical HNDT 14, would probably now be employed to produce a transparent image of the test object with a display of the internal deformities seen by this system. This could provide further verification of the (x,y) coordinates of flaws or suspect regions found by the optical HNDT subsystem 12. The processing system then analyzes the data from the two testing techniques and would most likely indicate that the correlation technique 16 be applied as a "fine turning" technique for the quantative analysis of flaws or deformities of those regions of interest.

The information obtained from these three subsystems would all be recorded on a single read-out, i.e., an optical square law recorder 18. The format presently configured for this recorder is a 70 mm film strip where each subsystem records its output on a single 70 mm frame. In the normal mode, a superposition of the holograms one on top of the other is not used, but rather a composite on one hologram or a three-frame sequence of 70 millimeters each are utilized.

If real time operation is to be achieved using this hybrid system, than a real time square law recording material such as photopolymer presently being developed by E. I. DuPont de Nemours and Company may be used. This photopolymer is capable of greater than 90% defraction efficiency at an exposure wavelength of 5145A, with a spatial frequency of up to 3000 l/mm. Further, this material satisfies the requirement of dry processing since it performs its development by the post exposure illumination of the photopolymer at the same wavelength as used for the exposure. With such a recording material, the information from all three subsystems could be recorded in real time.

Since each of these holographic HNDT subsystems could produce voluminous data, each in a separate format, which must be carefully analyzed before meaningful results can be obtained, an automatic processing system must be utilized. This task is handled by an optical scanning system 26 containing an image data receiver 20, an image data analyzer 22 and a mode indicator 24. The primary function of the optical scanner is to present at high speed in a digital computer input/output format, the spatial intensity data contained in a two-dimensional image input. The job of the optical scanning system 26 is complicated by the existence of three different data formats from the three different HNDT subsystems. Therefore, the image data receiver 20 must accept image information with superimposed interferometric fringe data from the optical HNDT system, transparent image information with superimposed internal flaws from the acousto-optical HNDT system and relative point intensity distributions from the correlation HNDT system.

A general system configuration for the optical scanning receiver/analyzer is provided in FIG. 2. The key element of the optical scanning system is the sensor 28 having support electronics 30 which must accept image data information from the three subsystems of the present hybrid system. This sensor 28 directly translates optical data format (input light distribution) into an electrical signal and passes this signal to an intensity function detector 32 which in turn translates this signal to provide the necessary input for an intensity function decoder 34, which in turn generates binary signal replicas for transmission to a standard digital computer 36. This system also includes a feedback network containing a scanning function decoder 48 which translates binary commands from the computer 36 into the necessary analog levels to cause a scanning function driver 46 to provide a sensor deflection field which is a precise replica of the scanning function decoder output.

The computer 36 contains an interactive display 40 which is an integral part of the mode indicator console 24, for supplying pertinent information to the operator interface/control of the entire integrated hybrid system. From this console, the operator has automated control of every subsystem of the integrated hybrid system. Therefore, the operator can cause one or all of the HNDT subsystems to perform its testing of the given test object. He has automated control of the formating of the optical square law detector 18 as well as memory (such as magnetic tape unit 38) to ascertain the precise position of a given 70 mm frame which may be needed for re-evaluation. Additionally, the operator has direct access to the digital computer 36 and its data content so as to interrogate the data analysis with several different techniques. After performing this data analysis, and the operator has not received a go/no go condition on the test objects, (this would result from predetermined threshholds for flaw deformity definition) he has the ability at the console to cause the HNDT subsystems to reinvestigate the test objects so as to acquire new test data under different loading or stressing criteria. The computer would also indicate that the same test procedure should be used, but that the test object is stressed in a different manner. Additionally, the digital computer 36 can be programmed to perform the duties of the operator, thereby resulting in a fully automatic system.

For a better understanding of the entire system, each of the subsystems will now be described in greater detail. FIG. 3 shows a schematic diagram of the optical HNDT subsystem which may use the real time analysis method, the double exposure method and/or the time averaging method. In real time holography, a single exposure of a photographic plate is made of an object in equilibrium at a reference point in time or condition or both. After development of the plate, said plate is placed back in the original recording position and the holographic system is again operated. This time, the test object is subjected to a measurable stress and viewed through the developed photographic plate. Any deformation of the object changes the phase of the light reflected from it and destructive interference takes place for points whose phase is changed by an odd multiple of 180°, i.e., path length change equal to one-half wavelength of the laser light providing the illumination for the system. This destructive interference is evidenced by dark and light bands or fringes, representative of half wavelength distances which appear across a virtual image on the photographic plate.

With double exposure holography, instead of merely viewing the object after deformation through the first developed exposure, a second exposure of the photographic plate is made after the object has been stressed. In this manner, two actual holograms are recorded on the plate and may be viewed by developing the plate, replacing the plate in the holographic system and illuminating the plate by the reference beam of the system. Two virtual images are formed because two exposures are made. Any deformations in the object between exposures causes the phase of the reflected light to differ which results in the same type of interference fringes referred to above.

Time averaging holography is primarily useful in analysis of periodic deformations of an object caused by vibration, and, typically, two successive exposures of a holographic plate of an object being vibrated enables two positions of the object to be recorded at or near the peaks of vibration because velocity is less in the region of the peaks. On development of the plate and reconstruction as in the case described above for double exposure holography, there will be provided interference between the wavefronts from the two virtual images causing fringe formation. Analysis of the fringes yields information of the shape and amplitude of the vibrating areas.

The optical HNDT embodied in FIG. 3 includes a laser 48 having an electronic shutter 50 controlled by shutter control 52 and having a power supply 42. The laser beam is either continuously or intermittently pulsed onto beam splitter 66 via mirror 60. This beam splitter allows for the formation of a reference beam 74 as well as a test beam 70. Through the use of mirrors 62, 64 and 80, the reference beam 74 is then projected onto a photographic plate after it has been reflected off of a test object 76 via mirrors 68 and 72. If the object is unstressed, an equilibrium hologram would be formed. The object 76 is then stressed by, for example, air supplied from air supply 54 through a pressure hose 58. A pressure gauge 56 is also included for measuring the amount of stress placed upon the object. In this manner, an optical hologram using either real time analysis, double exposure or time averaging can be formulated.

Figure 4:
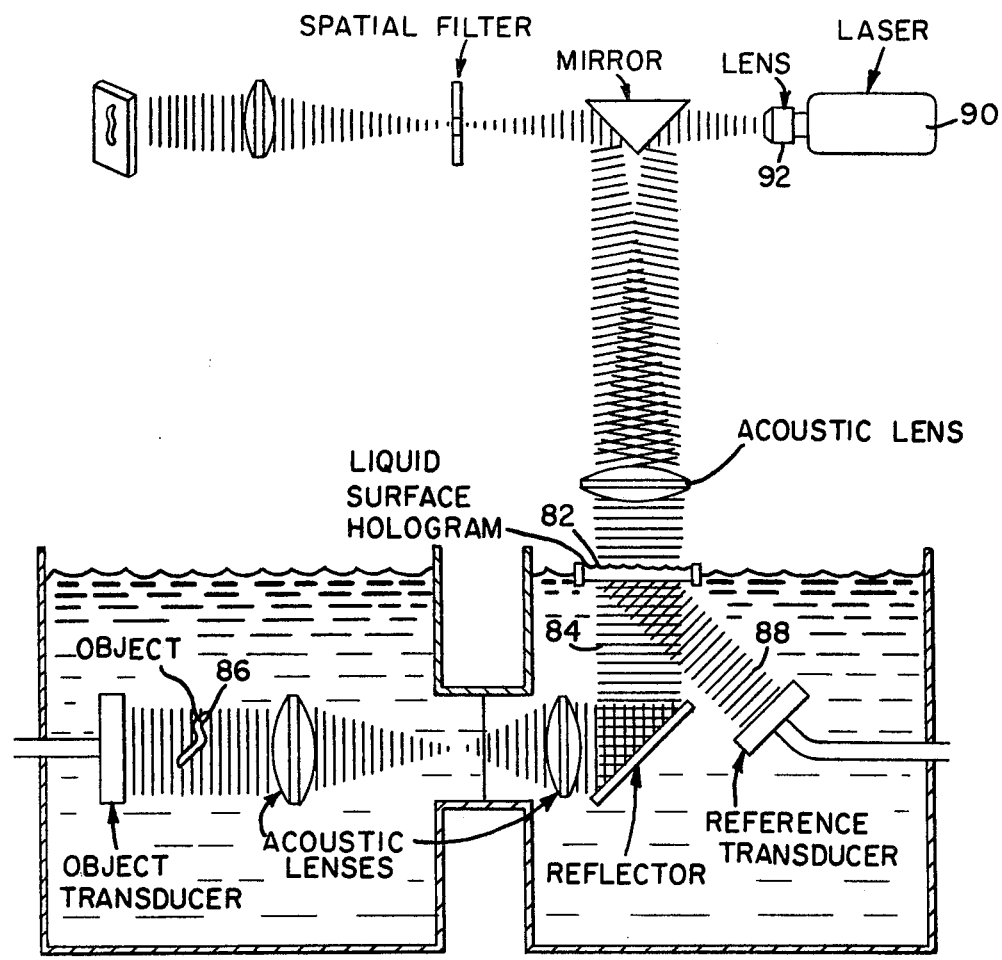
FIG. 4 is a schematic of an acouso/optical HNDT subsystem.

A schematic diagram of a representative immersion acousto-optical HNDT subsystem is depicted in FIG. 4. The "optical" aspect of this system derives from the fact that the acoustical modulation of the object beam will be recorded on an optical recorder. In other words, the object will be insonified with acoustic energy, then the acoustic wave, thus formed with modulation imposed during transmission through the object, is further used to modulate the object beam of an optical holographic system. Therefore, modulation of interest would be recorded optically, and this would provide the hybrid system with a single format detector/read out system as an input to the automatic data acquisition and analysis system.

The acoustical holography imaging system which is utilized by the present invention is shown in FIG. 4. Its method of operation employs a liquid surface hologram 82 for recording the acoustical interference pattern formed by an acoustical object beam 84 which transilluminates object 86, and a reference beam 88 which is coherent with the object beam. The interference pattern formed in the liquid surface interface 82 acts like a phase hologram, and reflection of laser light from laser 90 having lens 92 produces a real time acoustic image. This real time image may be viewed directly or recorded photographically. Successful imaging may be performed at the frequencies of, for example, 1, 3, 5 and 7 MHz.

Figure 5:
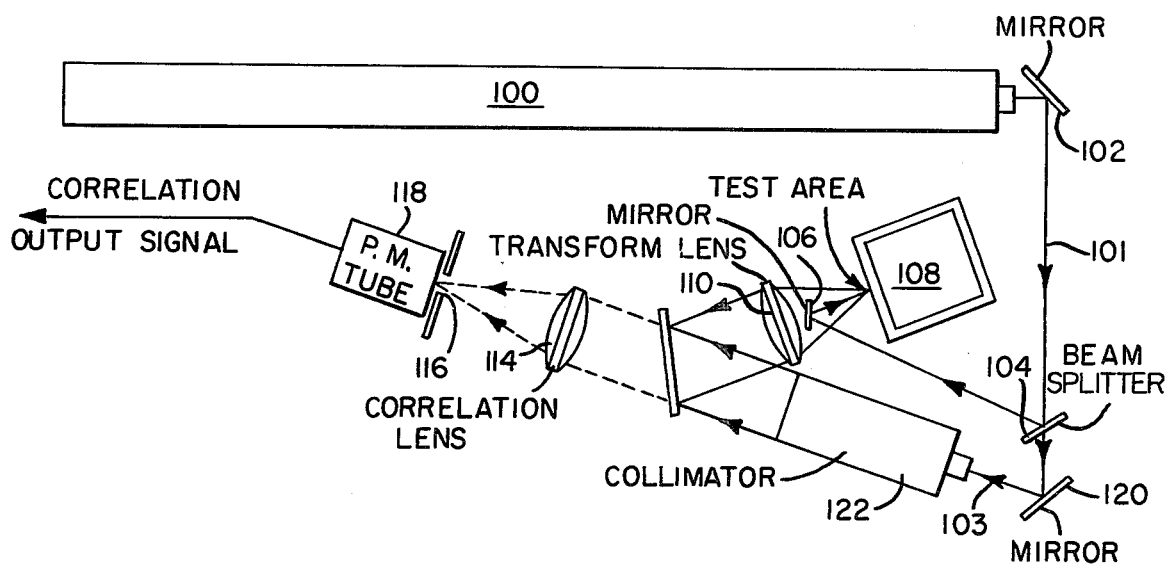
FIG. 5 is a schematic of a holographic correlation technique of the HNDT subsystem.

The correlation technique of the HNDT subsystem is shown in FIG. 5 and is also described in "Hybrid Design Provides HNDT with Automatic Data Processing", Part II, appearing in Holosphere, Volume 4, No. 6, June 1975. As shown in FIG. 5, a laser 100 produces a beam 101 which is reflected from mirrors 102 and 106 and beam splitter 104 onto a test area 108. When a test is being conducted, the wavefront $h(x,y)$ is back scattered off the test area 108 on a stressed object operated on by a transform lens 110 to produce its Fourier transform. A matched Vander Lugt filter is used to multiply $F[h(x,y)]$ by $F^*[s(x,y)]$, where $F[f(x,y)]$ represents the Fourier transform of $f(x,y)$ and $s(x,y)$ is the wavefront back scattered off the test area when the object is unstressed. The product $F[h(x,y)] F^*[x(x,y)]$ then is operated on by correlation lens 114 which results in the cross correlation of $h(x,y)$ and $s(x,y)$. The resultant output can be written as $$\int_{-\infty}^{+\infty} h(\xi, \eta) s^*(\xi - x, \eta - y) d\xi d\eta.$$

By placing an aperture 116 along the optical axis, the values $x$ and $y$ are chosen to be 0, yielding the final optical output:

$$\int_{-\infty}^{+\infty} h(\xi, \eta) s^* d\xi d\eta$$

This function is greatest when $h(x,y) = s(x,y)$, that is, when the object is unstressed. The function decreases rapidly as $h(x,y)$ differs from $s(x,y)$. A final output is detected by a photomultiplier tube 118 and monitored by a digital multimeter. A reference beam 103 produced by the laser beam traveling through beam splitter 104 and reflected off of mirror 120 to a collimator 122 and then onto the matched Vander Lugt filter 112 produces a complex amplitude distribution $R(x,y)$ resulting from the reference wavefront and the distribution resulting from the Fourier transform of the wavefront back scattered from the test area onto the unstressed object.

Therefore, if the amplitude transmittance is $T_a(x,y)$ then, $F[h(x,y)] T_a(x,y) = F[h(x,y)] F^*[s(x,y)]$.

Thus, we have formed a system which examines a test area on the object and gives an intensity reading which depends on how that area deforms as a whole on the stress. If the stressed area does not deform, the reading is at a maximum, but drops rapidly as the area deviates from its unstressed shape. It is assumed that faults deform anomalously under stress. Therefore, the object is scanned to seek test areas which give anomalous changes in intensity readings under controlled stress. Areas of interest will be determined by previous tests made with the optical and the acousto-optical HNDT subsystems. Thus, a holographic correlation subsystem will be used to "fine tune" the test results of the other two subsystems.

Consequently, it can be seen that the use of the three subsystems may be used in a hybrid system which gives comprehensive data relating to the flaws or debonds contained in a test object. In most cases, the test object will be initially scanned with the optical holographic technique, forming a hologram which will be analyzed by the digital computer. This output could, for example, indicate that there exists a possibility of subsurface flaws in the test object, and thus the automatic device would indicate that an acousto-optical holographic technique should be utilized. This technique would also produce a halogram which is interpreted by the prior processing system and might indicate a localized area of inhomogeneity. If this were the case, the computer would again indicate that more testing is needed, and then the correlation technique would be utilized to exactly affix the area of the flaws or debonds. Furthermore, even after all these techniques have been utilized, the data processor might indicate that still further testing is needed, and the object would be stressed in a different manner.

Many changes and modifications of the disclosed embodiment will be clear to anyone of ordinary skill in the art, and therefore the scope of the invention is not to be limited to exactly what is shown in the drawings and described in the specification. For example, the exact methods of forming the optical, acousto-optical and correlation techniques are not to be construed to be limited to the embodiments depicted in the present specification, but are to extend to other methods of performing this technique.

Additionally, since many of the components utilized in these techniques are quite similar (particularly those used in the optical and correlation techniques) a single apparatus may be employed which could carry out all three of the techniques after minor adjustments are made. This apparatus could be maintained on a movable platform or van which can be transported to the testing site, after which the required tests are performed. This van can carry a portable computer or may include an output terminal linking the van to a main computer terminal. This technique is especially useful in the on-site testing of rocket engines.

What is claimed is:

1. A hybrid non-destructive testing system for determining the presence of inhomogeneities in a test object comprising:
   (a) an optical testing subsystem selectively operable to produce image data information of the object in the form of an optical hologram for detecting surface or subsurface flaws;
   (b) an acousto/optical testing subsystem selectively operable to produce image data information of the object in the form of an optical hologram for detecting interior flaws;
   (c) a correlation testing subsystem selectively operable to produce image data information of the object in the form of an optical hologram for determining the exact location and magnitude of flaws whose presence has been determined by the results of selective operation of the other subsystems of the testing system;
   (d) real-time single format detector/read-out means for accepting image data information from the three subsystems; and
   (e) optical receiver/analyzer means for analyzing image data information accepted by the detector/read-out means.

2. A hybrid non-destructive testing system according to claim 1 wherein said detector/read-out means includes an optical square law recorder.

3. A hybrid non-destructive testing system in accordance with claim 2, said optical receiver/analyzer means includes sensor means for directly translating the optical format contained in said optical square law recorder into electrical signals.

4. A hybrid non-destructive testing system in accordance with claim 3, said output means further including a digital computer containing an interactive display, connected to said sensor means for analyzing the electrical signals.

5. A hybrid non-destructive testing system in accordance with claim 4, said output means further including a console mode indicator connected to said digital computer for indicating the results of the tests and whether sufficient data has been generated by said optical testing means, said acousto/optical testing means and said correlation testing means.

6. A non-destructive test method for determining the presence of inhomogeneities in a test object, comprising the steps of:
- determining the proper holographic test procedure to be performed on the test object, said procedure dependent upon the physical structure of the test object;
- performing said holographic test procedure on the test object, said test procedure producing an optical hologram automatically analyzing said optical hologram;
- determining if sufficient data is present to indicate the location of the inhomogeneities in the test object;
- ending the test procedure if sufficient data is available;
- determining the proper holographic test to be performed and under what stress conditions the test will be performed if sufficient data is not present to indicate the location of the inhomogeneities in the test object;
- performing the proper holographic test on the test object said test producing an optical hologram;
- automatically analyzing the data gathered from the holographic test procedures;
- determining if sufficient data is present to indicate the location of the inhomogeneities in the test object; and
- performing additional holographic test procedures determined from the analyzation of the data until sufficient data is obtained to indicate the location of the inhomogeneities in the test object.

7. The non-destructive test method according to claim 6 wherein an optical holographic test is initially performed on the test object, followed by an acousto-optical test on the test object, and then followed by a correlation test on the object.

* * * * *